(12) United States Patent
Alexander et al.

(10) Patent No.: US 7,766,960 B2
(45) Date of Patent: Aug. 3, 2010

(54) DELIVERY CATHETER THAT CONTROLS FORESHORTENING OF RIBBON-TYPE PROSTHESES AND METHODS OF MAKING AND USE

(75) Inventors: Miles Alexander, Fremont, CA (US); Todd Thompson, San Jose, CA (US); Tim Huynh, Santa Clara, CA (US); Ray Betelia, Santa Jose, CA (US)

(73) Assignee: NovoStent Corporation, Mountain View, CA (US)

( * ) Notice: Subject to any disclaimer, the term of this patent is extended or adjusted under 35 U.S.C. 154(b) by 545 days.

(21) Appl. No.: 10/836,909

(22) Filed: Apr. 30, 2004

(65) Prior Publication Data

US 2005/0246010 A1 Nov. 3, 2005

(51) Int. Cl.
*A61F 2/00* (2006.01)
*A61F 2/06* (2006.01)

(52) U.S. Cl. ............ 623/1.22; 623/1.15; 623/1.11

(58) Field of Classification Search ........ 623/1.11, 623/1.12, 1.22, 1.15; 606/108, 194; 604/103.09
See application file for complete search history.

(56) References Cited

U.S. PATENT DOCUMENTS

| | | | | |
|---|---|---|---|---|
| 4,541,681 A | * | 9/1985 | Dorman et al. | 439/429 |
| 4,553,545 A | | 11/1985 | Maass et al. | |
| 4,760,849 A | | 8/1988 | Kropf | |
| 4,768,507 A | * | 9/1988 | Fischell et al. | 623/1.11 |
| 5,129,910 A | * | 7/1992 | Phan et al. | 606/127 |
| 5,234,437 A | * | 8/1993 | Sepetka | 606/194 |
| 5,634,928 A | * | 6/1997 | Fischell et al. | 623/1.11 |
| 5,824,052 A | | 10/1998 | Khosravi et al. | |
| 5,824,053 A | | 10/1998 | Khosravi et al. | |
| 6,425,915 B1 | | 7/2002 | Khosravi et al. | |
| 6,478,813 B1 | | 11/2002 | Keith et al. | |
| 6,607,551 B1 | * | 8/2003 | Sullivan et al. | 623/1.11 |
| 6,736,844 B1 | | 5/2004 | Glatt et al. | |
| 7,060,088 B1 | * | 6/2006 | Fischell et al. | 623/1.15 |
| 7,226,472 B2 | * | 6/2007 | Pederson et al. | 623/1.11 |
| 2003/0069633 A1 | * | 4/2003 | Richter et al. | 623/1.22 |

FOREIGN PATENT DOCUMENTS

WO 2005/110284 11/2005

OTHER PUBLICATIONS

Final Office Action mailed Nov. 27, 2007; U.S. Appl. No. 10/772,764, filed Feb. 4, 2004.

* cited by examiner

*Primary Examiner*—Anhtuan T Nguyen
*Assistant Examiner*—Amy T Lang
(74) *Attorney, Agent, or Firm*—James F. Hann; Haynes Beffel & Wolfeld LLP

(57) ABSTRACT

The present invention is directed to a delivery catheter for use in deploying a vascular prosthesis having a self-expanding helical section for use in a wide range of interventional applications. The delivery catheter comprises an elongated member having a helical ledge with a pitch selected to impose a predetermined amount of foreshortening on the vascular prosthesis during deployment. Methods of making and using the delivery catheter of the present invention also are provided.

16 Claims, 4 Drawing Sheets

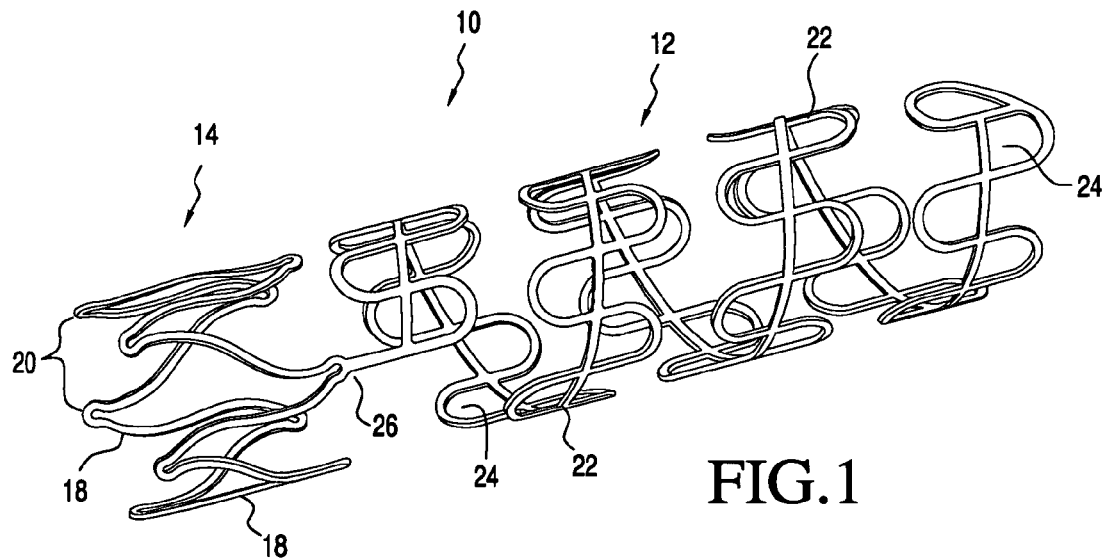
FIG.1
FIG.2
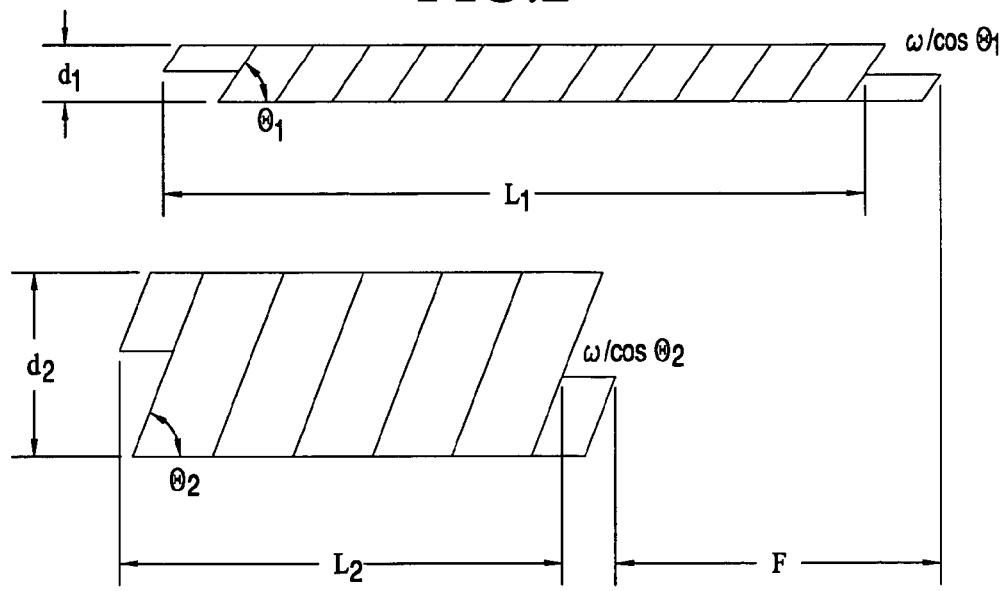

DELIVERY CATHETER THAT CONTROLS FORESHORTENING OF RIBBON-TYPE PROSTHESES AND METHODS OF MAKING AND USE

FIELD OF THE INVENTION

The present invention relates to a delivery catheter, and methods of use, for an implantable vascular ribbon-type prosthesis having a helical section and at least one anchor section, wherein the delivery system controls foreshortening of the prosthesis during deployment.

BACKGROUND OF THE INVENTION

Today there are a wide range of intravascular prostheses on the market for use in the treatment of aneurysms, stenosis, and other vascular irregularities. Balloon expandable and self-expanding stents are well known for restoring patency in a stenosed vessel, e.g., after an angioplasty procedure, and the use of coils and stents are known techniques for treating aneurysms.

Previously-known self-expanding stents generally are retained in a contracted delivery configuration using a sheath, then self-expand when the sheath is retracted. Such stents commonly have several drawbacks, for example, the stents may experience large length changes during expansion (referred to as "foreshortening") and may shift within the vessel prior to engaging the vessel wall, resulting in improper placement. Additionally, many self-expanding stents have relatively large delivery profiles because the configuration of their struts limits further compression of the stent. Accordingly, such stents may not be suitable for use in smaller vessels, such as cerebral vessels and coronary arteries.

Other drawbacks associated with the use of coils or stents in the treatment of aneurysms is that the devices, when deployed, may have a tendency to straighten or otherwise remodel a delicate cerebral vessel, which may cause further adverse consequences. Moreover, such devices may not adequately reduce blood flow from the cerebral vessel into the sac of the aneurysm, which may increase the likelihood of rupture.

For example, PCT Publication WO 00/62711 to Rivelli describes a stent comprising a helical mesh coil having a plurality of turns and including a lattice having a multiplicity of pores. The lattice is tapered along its length. In operation, the plurality of turns are wound into a reduced diameter helical shape, then constrained within a delivery sheath. The delivery sheath is retracted to expose the distal section of the stent and anchor the distal end of the stent. As the delivery sheath is further retracted, subsequent individual turns of the stent unwind to conform to the diameter of the vessel wall.

The stent described in the foregoing publication has several drawbacks. For example, due to friction between the turns and the sheath, the individual turns of the stent may bunch up, or overlap with one another, when the delivery sheath is retracted. U.S. Pat. No. 4,768,507 to Fischell et al. and U.S. Pat. No. 6,576,006 to Limon et al., each describe the use of a groove disposed on an outer surface of an interior portion of the stent delivery catheter, wherein at least a portion of the stent is disposed within the groove to prevent axial movement during proximal retraction of the sheath.

While the delivery catheters disclosed in the foregoing patents prevent axial movement and bunching of the prosthesis during retraction of the sheath of the delivery catheter, those systems do not effectively address the issue of stent foreshortening. In particular, once the sheath of the delivery catheter is fully retracted, the turns of a ribbon-type stent may shift relative to one another within the vessel prior to engaging the vessel wall, resulting in inadequate coverage of the stenosis.

In view of the drawbacks of previously known ribbon-type stent delivery systems, it would be desirable to provide a delivery catheter that controls axial movement of a ribbon-type stent within the catheter during deployment.

It also would be desirable to provide a delivery catheter suitable for use with ribbon-type stents that provides a predictable amount of foreshortening of the stent during delivery, thereby improving accuracy of stent deployment.

It further would be desirable to provide a delivery catheter suitable for use with ribbon-type stents that mitigates foreshortening of the stent during delivery, and thus enhances the ability of a stent of predetermined length to provide adequate coverage of a stenosis.

SUMMARY OF THE INVENTION

In view of the foregoing, it is an object of the present invention to provide a delivery catheter for use with a ribbon-type stent that controls axial movement of the stent within the catheter during deployment.

It is another object of this invention to provide a delivery catheter suitable for use with ribbon-type stents that provides a predictable amount of foreshortening of the stent during delivery, thereby improving accuracy of stent deployment.

It is a further object of the present invention to provide a delivery catheter suitable for use with ribbon-type stents that mitigates foreshortening of the stent during delivery, and thus enhances the ability of a stent of predetermined length to provide adequate coverage within of a stenosis.

These and other objects of the present invention are accomplished by providing a delivery catheter for use with a ribbon-type stent comprising an inner member slidably disposed within a sheath. In accordance with the principles of the present invention, the inner member includes a helical ledge that causes the stent to be wound around the inner member with a pitch selected to provide a preselected amount of foreshortening of the stent during deployment, including substantially zero foreshortening.

In one embodiment, the delivery catheter includes an inner member comprising a elongated flexible shaft having a helical wire affixed to its exterior surface, wherein the pitch of the helical wire is preselected for the stent to be delivered. The size of the gap between adjacent turns of the helical wire preferably causes the adjacent turns of the ribbon-type stent, when wound about the inner member, to overlap. The helical wire provides a ledge or abutment surface against which the ribbon-type stent may be urged during winding of the stent to its reduced-diameter delivery configuration. The helical wire may be arranged so either the proximal-facing or distal-facing surface of the helical wire defines the ledge.

Alternatively, the inner member may have the abutment surface integrally formed with the exterior surface of the inner member. This may be accomplished by braiding a plurality of wire strands together, wherein one of the wire strands has a larger cross-section than the others. In this case, the larger cross-section wire protrudes from the inner member to define the helical ledge on the surface of the inner member. As a further alternative, the helical ledge may be integrally formed with an inner member formed from a suitable polymer, e.g., by extrusion or molding.

The delivery catheter of the present invention optionally may include an inflatable balloon disposed adjacent to the distal end of the inner member, and distal to the distal end of the sheath. When so provided, the inflatable balloon may be deployed to engage a portion of a vessel so that proximal withdrawal of the sheath does not inadvertently result in axial displacement of the delivery catheter or stent relative to the vessel. Advantageously, the balloon distributes the load created by proximal withdrawal of the sheath uniformly to the circumference of the vessel, thereby reducing local stress concentrations during deployment of the stent that might otherwise arise where a partially-deployed stent contacts the vessel wall. The inner member may in addition include means for engaging a distal section of the stent against axial displacement during proximal retraction of the sheath.

Methods of making and using the delivery catheter of the present invention also are provided.

BRIEF DESCRIPTION OF THE DRAWINGS

Further features of the invention, its nature and various advantages will be more apparent from the accompanying drawings and the following detailed description of the preferred embodiments, in which:

FIG. 1 is a perspective view of a vascular prosthesis suitable for use with the delivery catheter of the present invention;

FIG. 2 is a drawing depicting foreshortening of a ribbon-type stent as encountered with previously-known delivery systems as the stent expands from a contracted delivery configuration to an expanded deployed configuration;

DETAILED DESCRIPTION OF THE INVENTION

Figure 3:
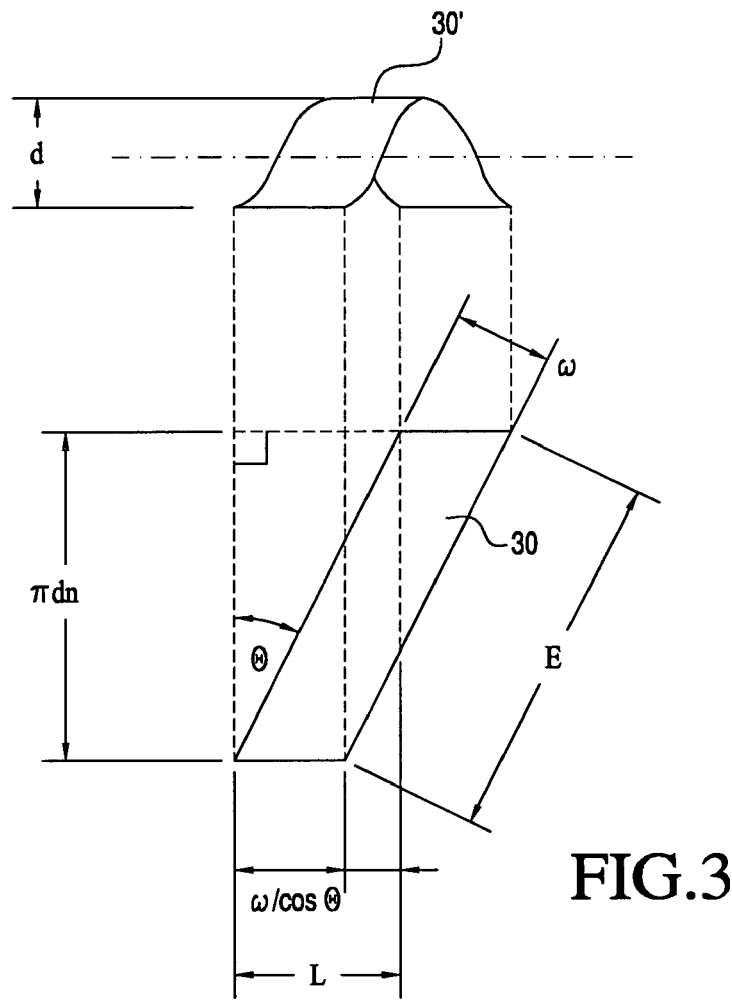
FIG. 3 is a drawing depicting a ribbon-type stent unrolled to a flat configuration and projected onto an expanded deployed configuration (for clarity, only a single turn is shown, although it will be understood that in the deployed configuration the stent includes multiple turns)

The present invention is directed to a delivery catheter for use with an implantable vascular prosthesis configured for use in a wide range of applications, such as treating aneurysms, maintaining patency in a vessel, and allowing for the controlled delivery of therapeutic agents to a vessel wall. Advantageously, the delivery catheter of the present invention may be used to deliver a vascular prosthesis having a helical ribbon portion joined, at its distal end, to a radially self-expanding anchor portion, such as depicted in FIG. 1. The delivery catheter provides enhanced accuracy in delivering the stent by providing a predictable degree of foreshortening of the stent, including substantially zero foreshortening. Additionally, the delivery catheter optionally may include a balloon that reduces inadvertent axial movement of the delivery catheter during stent deployment and/or means that reduce axial displacement of the vascular prosthesis relative to the delivery catheter.

Referring to FIG. 1, a preferred vascular prosthesis suitable for use with the delivery catheter of the present invention is described. As used in this specification, the terms "vascular prosthesis" and "stent" are used interchangeably. Vascular prosthesis 10 is described in copending commonly assigned U.S. patent application Ser. No. 10/342,427, filed Jan. 13, 2003, and comprises helical section 12 and distal section 14, each capable of assuming contracted and deployed states. In FIG. 1, helical section 12 and distal section 14 are each depicted in their respective deployed states.

Vascular prosthesis 10 preferably is formed from a solid tubular member comprising a shape memory material, such as nickel-titanium alloy (commonly known in the art as Nitinol). The solid tubular member then is laser cut, using techniques that are per se known in the art, to a desired deployed configuration, as depicted in FIG. 1. An appropriate heat treatment, per se known in the art, then may be applied to vascular prosthesis 10 while the device is held in the desired deployed configuration (e.g., on a mandrel), thus conferring a desired deployed configuration to vascular prosthesis 10 when self-deployed.

Distal section 14 preferably has a generally zig-zag configuration in the deployed state, wherein the zig-zag configuration preferably is formed by laser cutting a solid tube to form a pattern comprising plurality of arcuate struts 18 joined at apices 20. Distal section 14 is designed to be deployed from the delivery catheter of the present invention first to fix the distal end of the stent at a desired known location within a vessel. In this manner, subsequent deployment of helical section 12 of the stent may be accomplished with greater accuracy.

Helical section 12 preferably comprises a helical mesh configuration that includes a plurality of substantially flat turns 22. Plurality of turns 22 may include a multiplicity of openings, as illustrated by openings 24. It should be understood that the configuration of helical section 12 depicted in FIG. 1 is merely illustrative, and other patterns may be advantageously employed. Helical section 12 is coupled to distal section 14 at junction 26.

Referring now to FIG. 2, the problem of stent foreshortening as heretofore encountered with ribbon-type stents is described. As used in this specification, "foreshortening" refers to the length change of the stent between its contracted delivery configuration and its expanded deployed configuration. More specifically, the contracted delivery configuration, depicted in the upper portion of FIG. 2, corresponds to the state wherein consecutive turns of the stent have been tightly wrapped around adjacent turns to reduced the diameter of the stent to diameter $d_1$ and length of $L_1$, suitable for transluminal delivery to a target location within a vessel. In the deployed configuration, the stent is permitted to expand to its nominal working diameter, and has a diameter $d_2$ and length of $L_2$, suitable for supporting a target location within a vessel. "Foreshortening" is defined as the difference between the lengths $L_1$ and $L_2$.

In most interventional procedures, satisfactory stent placement requires predictable placement of the distal and proximal ends of the stent within a target vessel. Previously-known ribbon-type self-deploying stents, however, have encountered limited clinical acceptance due to problems associated with foreshortening and inaccurate placement.

Specifically, previously-known ribbon-type stents often are wound down around a delivery catheter in either an "edge to edge" manner (where the edges of adjacent turns lie next to one another) or with an overlap (or "shingled"), and then covered with a sheath that restrains the stent in the contracted delivery configuration. When wound "edge to edge," the stent may be significantly longer in the contracted delivery configuration than in the deployed configuration, and thus result in significant foreshortening when deployed.

On the other hand, when the turns of the stent are permitted to overlap in the contracted delivery configuration, the turns of the stent may lock or bind within the delivery system during deployment. Further still, in either method of contracting the stent to its contracted delivery configuration, the stent has a tendency to jump or hop forwards or backwards when deployed, resulting in poor control. Thus, previously-known ribbon-type stents generally are perceived to be capable of less accurate deployment than conventional balloon expandable stents.

Vascular prosthesis 10 of FIG. 1 is designed to address the issue of movement of the distal end of the stent. In particular, distal section 10 functions as a anchor that fixes the distal end of the stent to the vessel wall. The delivery catheter of the present invention provides the rest of the solution to the placement problem by controlling winding of the stent to a predetermined contracted delivery configuration, and likewise controlling unwinding of the stent during deployment to mitigate foreshortening.

In accordance with the principles of the present invention, it has been discovered that certain trigonometric relationships may be utilized whereby the sent may be wrapped to its reduced delivery diameter, and experience little or no foreshortening during deployment. These relationships are derived below, and then implemented in the delivery catheters of the present invention, as set forth below.

Referring now to the lower portion of FIG. 3, 30 previously-known ribbon-type stent is depicted in an unrolled, flattened configuration. When deployed, as schematically depicted by the single turn in the upper portion of the FIG. 3, the stent 30' comprises a strip of material wrapped cylindrically at a diameter (d) over an axial length (L) for a number of revolutions (n). The strip is wrapped at a wrap angle ($\theta$), which may be measured from a plane normal to the axis of the helix.

The strip has a width ($\omega$) and an edge length (E); these are physical characteristics of the stent that do not change. On the other hand, the diameter (d), wrap angle ($\theta$), number of revolutions (n), and axial length (L) are interrelated characteristics that vary depending upon the helical configuration of the stent. For example, the diameter of the stent varies between the contracted delivery configuration and deployed configuration, which as shown in FIG. 2 also may effect the wrap angle, number of revolutions, and axial length.

Figure 4:
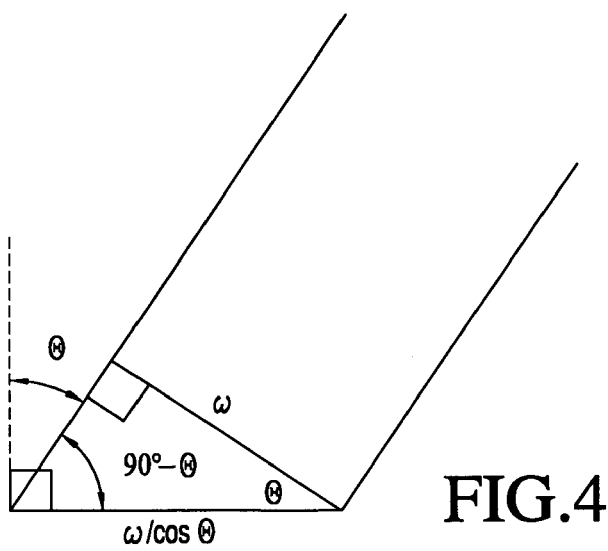
FIG. 4 is a drawing depicting trigonometric relationships between the wrap angle of the stent of FIG. 3 and width of the stent.

From inspection of FIG. 3, it can be seen that the axial length of the stent in the helical configuration is L plus the proximal-most part of the projected strip width. This additional length may be computed as depicted in FIG. 4, using a right triangle in which one leg is the strip width ($\omega$), and the hypotenuse is the strip width projected onto the helical axis of the stent. Because the angle on the right side of this triangle is equal to the wrap angle ($\theta$), the strip width projected onto the helical axis of the stent is equal to $\omega/\cos \theta$. The total length of the stent in the helical configuration is therefore $L+\omega/\cos \theta$. In addition, it will be observed that, as wrap angle $\theta$ increases, the projected width of the strip also increases.

Referring now to FIGS. 2 and 3, foreshortening may be computed as the change in the axial length of the stent as it transitions from one diameter ($d_1$) to another ($d_2$) during deployment:

$$F=(L_1+\omega/\cos \theta_1)-(L_2+\omega/\cos \theta_2)$$

$$F=(L_1-L_2)+(\omega/\cos \theta_1-\omega/\cos \theta_2)$$

From inspection of FIG. 3, it can be seen that edge length E, axial length L and wrap angle $\theta$ are related by the trigonometric relationship:

$$L=E \sin \theta$$

Substituting this relationship into foregoing equation for foreshortening provides:

$$F=(E \sin \theta_1-E \sin \theta_2)+(\omega/\cos \theta_1-\omega/\cos \theta_2)$$

$$F=E(\sin \theta_1-\sin \theta_2)+\omega(1/\cos \theta_1-1/\cos \theta_2)$$

Of primary interest in the context of the present invention is the case where there is no foreshortening (F=0) when the stent transitions from diameter $d_1$ to diameter $d_2$. By setting the above equation equal to zero, it will be observed that the edge component of the equation $E(\sin \theta_1-\sin \theta_2)$ and the width component $\omega(1/\cos \theta_1-1/\cos \theta_2)$ must either be equal to zero, or be equal and opposite. For meaningful wrap angles ($0<\theta<90$), both components will always have the same sign. Thus, in order for the equation to balance, both components of the equation must be equal to zero. This leads to the conclusion that for there to be no foreshortening during stent deployment, the two wrap angles must be equal: $\theta_1=\theta_2$. Accordingly, for a stent wrapped into a helical configuration, where strip width $\omega$ and total edge length E are constant, the amount of foreshortening between two different configurations is dependant on wrap angle alone. Thus, to eliminate foreshortening between any two helical configurations, both configurations must have the same wrap angle $\theta$.

Figure 5:
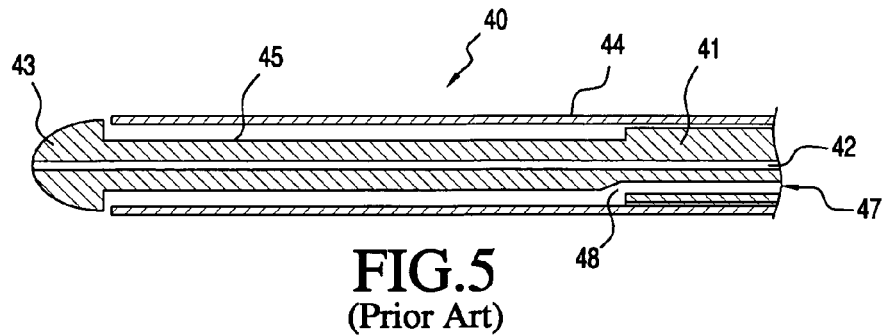
FIG. 5 is a side sectional view of a prior art delivery system having an inner member disposed within a sheath for relative sliding motion therebetween.

Referring to FIG. 5, previously-known delivery catheter 40 suitable for use in deploying a ribbon-type stent is described. Delivery catheter 40 is disclosed, e.g., in U.S. Pat. No. 4,665, 918 to Garza et al., and includes inner member 41 having central lumen 42, nose cone 43 and sheath 44. Catheter 41 includes recessed portion 45 that cooperates with sheath 44 to retain the stent in its contracted delivery configuration for transluminal delivery. Delivery catheter 40 also may comprise fluid delivery lumen 47, which may be used to deliver chilled saline via one or more ports 48 to the stent during delivery.

Figure 6:
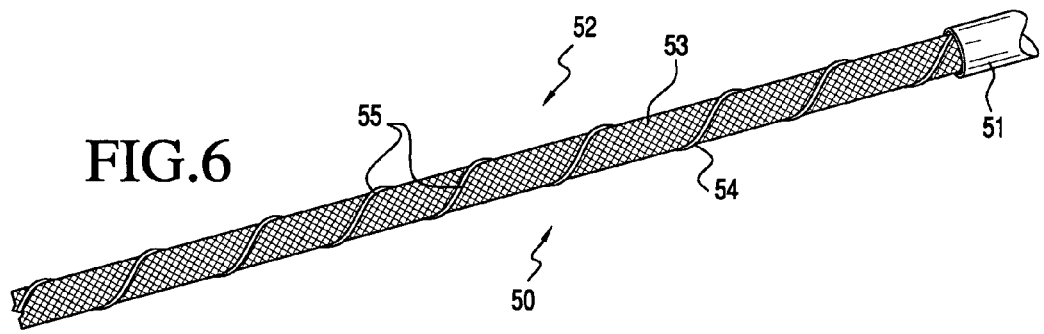
FIG. 6 is a perspective view of a distal portion of an inner member for a delivery catheter constructed in accordance with the principles of the present invention.

With respect to FIG. 6, delivery catheter 50, constructed in accordance with the principles of the present invention, is described. Delivery catheter 50 includes sheath 51 and inner member 52 that implements the rule described hereinabove to mitigate or eliminate foreshortening by imposing on the stent, by imposing on the stent in the contracted delivery configuration the wrap angle $\theta$ that the stent will have in the deployed configuration.

Inner member 52 illustratively comprises braided wire tube 53 having helical wire 54 affixed to its outer surface to form helical ledge 55, for example, using a biocompatible adhesive or solder. Alternatively, helical wire 54 may be laminated to the outer surface of braided wire tube 53 using a polymeric layer, or inner member 52 itself may be formed by sandwiching a helical wire between inner and outer polymeric layers. During wrapping of a stent onto inner member 52, either a proximal or distal edge of the stent is abutted against helical ledge 55, so that adjacent turns of the stent overlap one another. Alternatively, braided tube 53 and helical wire 54 could be replaced with an inner member having an exterior surface including an integrally formed ridge. In addition, helical ledge 55 could be formed by other features such as protrusions extending from the surface of the inner member.

Provision of the helical ledge directly on the exterior surface of the inner member as in the embodiment of FIG. 6 permits a definable deployment length of the stent, namely, zero foreshortening. Advantageously, the helical ledge also provides linear resistance to stent migration when sheath 51 is retracted during stent deployment. This engagement between the turns of the stent and the inner member maintains the linear stability of the stent, and reduces the risk that overlapping turns of the stent do not bunch up or seize against the interior surface of the sheath. Moreover, the helical ledge ensures that the stent unwinds on its axis but does not experience significant linear change along the axis.

Use of the delivery catheter of FIG. 6 is as follows: starting at one end of the stent and helical ledge 55, the stent is wound around the inner member to its contracted delivery configuration while an edge of the stent is abutted against ledge 55. This causes each subsequent turn of the stent to overlap the preceding turn. The amount of overlap of adjacent turns of the stent is defined by the helical ledge, and is a feature of the particular design of the stent. When the stent is wound down to its contracted delivery configuration, sheath 51 is advanced over the stent and inner member to retain the stent in its contracted delivery configuration. When loaded in the delivery catheter, the length of the stent is the same as the length of the stent in the deployed configuration.

The specific steps for winding the stent onto the inner member in a proximal to distal direction are as follows: First, the tail of the stent is located and fixed at the proximal end of the stent area of the inner member with the distal edge of the stent abutted against the helical ledge. Next, the stent is wrapped around the inner member using the helical ledge to control the pitch and overlap of the stent. The sheath is then slid over the stent while being rotated in a direction in which the stent is wrapped. Finally, if a stent as depicted in FIG. 1 is employed, the anchor portion of the stent is crimped down, and the sheath is slid over the anchor portion to retain the stent in the contracted delivery configuration. When loaded into the delivery catheter in this manner, the helical ledge guides the pitch of the stent as it is wrapped, thus providing a zero foreshortening solution.

While the foregoing method of employing the delivery catheter of the present invention mitigates foreshortening, it does not prevent each individual turn of the stent from sliding proximally with the sheath during stent deployment. Accordingly, another method of using delivery catheter 50 calls for winding the stent onto the inner member in a distal to proximal direction, as follows: First, the anchor portion of the stent is placed on inner member in a desired location, and the joint between anchor portion and the helical body portion of the stent is temporarily fixed to the inner member.

Next, the proximal portion of the stent is wrapped around the inner member, wherein the proximal edge of the stent is abutted against the helical ledge. When the stent is completely wrapped around the inner member, the sheath is slid over the stent and inner member while rotating the sheath in the direction in which the stent is wound. The sheath is advanced up to the joint where the distal anchor portion of the stent is coupled to the helical proximal portion. The anchor portion then is crimped down onto the inner member, and the sheath is advanced, while being rotated in the direction of the wrap, until it covers the anchor portion. When the stent is loaded in accordance with this method of the present invention, the helical ledge not only mitigates foreshortening, but in addition, the proximal edge of the stent is prevented from sliding in the proximal direction during retraction of the sheath to deploy the stent.

Figure 7:
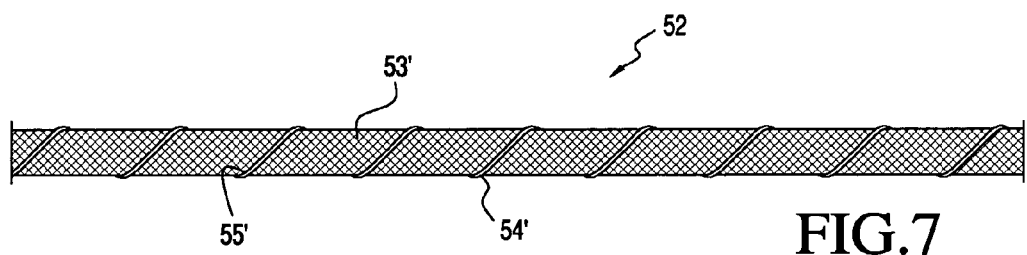
FIG. 7 is a side view of a distal portion of another inner member of a delivery catheter of the present invention, wherein the helical ledge is integrally formed with the inner member.

Referring now to FIG. 7, alternative inner member 52' of the present invention is described. Inner member 52' also preferably comprises an elongated braided tube 53' having helical wire 54' integrally formed with the tube to define helical ledge 55'. Braid 53' preferably is sandwiched between polymeric inner and outer liners, and is made up of a plurality of wire members braided together around the inner liner. The wires used to construct braid 53' may have flat or round wires cross-sections, and may comprise stainless steel or polymeric strands, e.g., such as polyester or Kevlar, depending on the flexibility and rigidity desired for inner member 53'. In addition, the rigidity of the inner member may be further selected by choice of the wire diameter, number used and the tightness of the pitch of the braid.

Helical ledge 55' is formed by increasing the diameter of one of the wires used to construct the braid of tube 53', so that it protrudes from the exterior surface of the completed inner member. In particular, the number of braid members and the tightness of their pitch may be selected so that helical wire 54' forms helical ledge 55' that imposes a selected wrap angle on the stent when wound in accordance with the above-described methods. As a further alternative, the inner member may be formed of a polymeric material so that its exterior surface includes an integrally formed ledge, e.g., by extrusion or molding.

Inner member 52' of FIG. 7 permits the delivery catheter to be easily customized during manufacture to provide a desired degree of foreshortening of the stent, including zero foreshortening. In addition, inner member 52' avoids the manufacturing difficulties inherent in the design of FIG. 6, by eliminating the step of affixing the helical wire to the inner member. Still further, inclusion of helical wire 54' in braided tube 53' over the length of the inner member advantageously provides for better interaction between the inner member and sheath by providing fewer points of contact therebetween and therefore less frictional engagement between the two members.

Further in accordance with the principles of the present invention, it is possible to adjust the pitch of the helical ledge that imposes the wrap angle on the stent in the contracted delivery configuration to provide a desired degree of foreshortening of the stent during deployment, including the option of having the stent increase in length. Returning to the analytical framework set forth above, a foreshortening ratio (f) may be defined as the ratio of axial length lost during deployment of the stent. This term may be defined mathematically as:

$$f = \frac{\left(\frac{L_1 + \omega}{\cos\theta_1}\right) - \left(\frac{L_2 + \omega}{\cos\theta_2}\right)}{\frac{L_1 + \omega}{\cos\theta_1}}$$

Because the change in projected body width is generally small compared to the change in axial length of the stent, the foregoing equation may be simplified by neglecting the proximal projected strip width terms, resulting in:

$$f = \frac{L_1 - L_2}{L_1}$$

Again substituting

L=E sin θ into the above equation yields:

$$f = \frac{L_1 - L_2}{L_1} = \frac{E\sin\theta_1 - E\sin\theta_2}{E\sin\theta_1} = \frac{\sin\theta_1 - \sin\theta_2}{\sin\theta_1}$$

$$f = 1 - \frac{\sin\theta_2}{\sin\theta_1}$$

Thus, the amount of foreshortening between two different helical configurations may be determined by selection of the wrap angles $\theta_1$ and $\theta_2$ to provide any desired degree of foreshortening or length increase of the stent as may be desired.

In addition to the above-noted potential issues with ribbon-type stents, it also is possible that movement of the sheath of the delivery catheter may inadvertently cause the delivery catheter to translate proximally within the vessel prior to deployment of the prosthesis, thereby leading to reduced accuracy of the stent placement. In accordance with yet another aspect of the present invention, the delivery catheter of the present invention is configured to reduce the possibility of inadvertent axial translation of the delivery catheter during an initial phase of stent deployment, i.e., prior to deployment of distal section 14 of the stent of FIG. 1.

Figure 8:
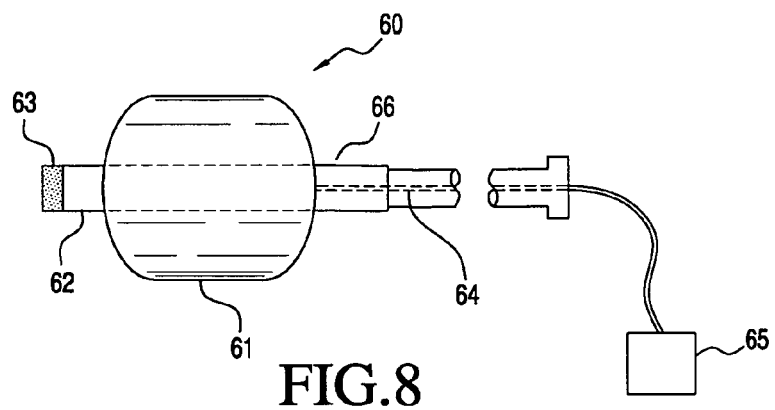
FIG. 8 is a side view illustrating an optional balloon that may be used with the delivery catheter of the present invention to enhance stent placement.

Referring now to FIG. 8, inner member 60 of the present invention includes a portion defining a helical ledge, as in the embodiments of FIGS. 5 and 6, and further comprising optional balloon 61 disposed adjacent to distal end 62. Radio-opaque marker 63 is affixed to the distal end of inner member 60 to make the distal end of the inner member visible under fluoroscopic imaging. Balloon 61 may be formed from compliant or semi-compliant materials, such as nylon or PEBAX, and is inflated via 64. Lumen 64 may be pressurized with fluid from syringe or inflator 65, which may be selectively coupled to the proximal end of inner member 60, as is known in the art.

In accordance with this aspect of the present invention, inner member 60 further includes means for engaging the distal end of the distal section of stent 10. In one preferred embodiment, the means for engaging comprises polymer layer 66 that has been treated, e.g., by formulation, mechanical abrasion, chemically or by heat treatment, to make the polymer tacky or otherwise enhance the grip of the material. Preferably polymer layer 66 comprises a proximal shoulder of balloon 62, although the polymer layer alternatively may be formed and applied separately from balloon 61. Alternatively, balloon 61 may be omitted, and polymer layer 66 may be disposed on a portion of the inner member adjacent the distal end 62.

In operation, the delivery catheter of the present invention, including inner member 60, is advanced along a guide wire into a vessel containing a treatment area. Positioning of the vascular prosthesis relative to the treatment area is confirmed using radio-opaque marker 63. Once the delivery catheter is placed in the desired location, sheath 51 (see FIG. 6) is retracted proximally to permit distal section 14 of stent 10 to deploy. In accordance with the principles of the present invention, polymer layer 66 grips distal section 14 of stent 10, thereby preventing distal section 14 from being dragged proximally into engagement with helical section 12 during retraction of the sheath. Instead, polymer section 66 grips distal section 14 against axial movement, and permits the distal section to expand radially outward into engagement with the vessel wall once the sheath is retracted.

In addition, either before or after distal section 14 is expanded into engagement with the vessel wall, balloon 61 may be expanded to contact the vessel wall. Balloon 61 therefore anchors distal end 63 of the delivery catheter relative to the vessel wall, so that no inadvertent axial displacement of the delivery catheter arises during proximal retraction of the sheath to release distal section 14 or helical section 12 of stent 10.

Referring now to FIGS. 9A to 9D, methods of using delivery catheter 70 of the present invention are described to deliver a stent of the type shown in FIG. 1. Stent 80 is disposed in its delivery configuration compressed around inner member 72 having a helical ledge, and retained by sheath 71. Distal section 81 of stent 80 is disposed in contact with polymer layer 73 to prevent relative axial movement therebetween.

Figure 9A:
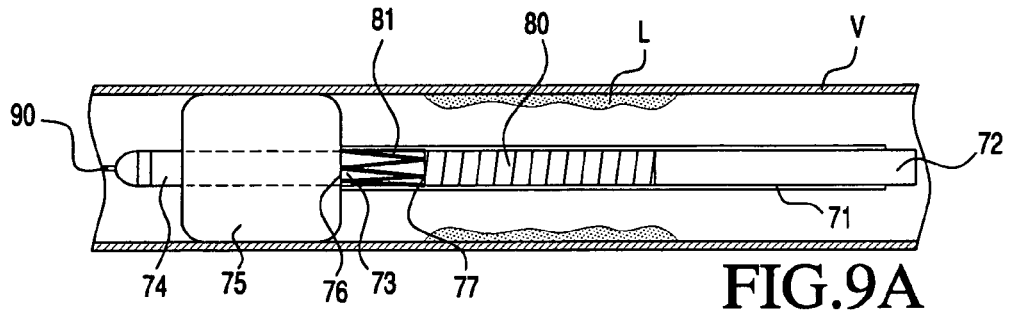
FIGS. 9A to 9D are side-sectional views showing a method of delivering the vascular prosthesis of FIG. 1 using the delivery catheter of the present invention.

As shown in FIG. 9A, delivery catheter 70 is percutaneously and transluminally advanced along guide wire 90 until tip 74 of the catheter is disposed within adjacent healthy tissue of vessel V, distal of lesion L, e.g., as determined by fluoroscopic imaging. Balloon 75 then is inflated to engage the vessel wall and prevent axial displacement of the delivery catheter during subsequent retraction of sheath 71. Polymer layer 73 engages distal section 81 of stent 80, thereby preventing axial displacement of distal section 81 during retraction of sheath 71.

Figure 9B:
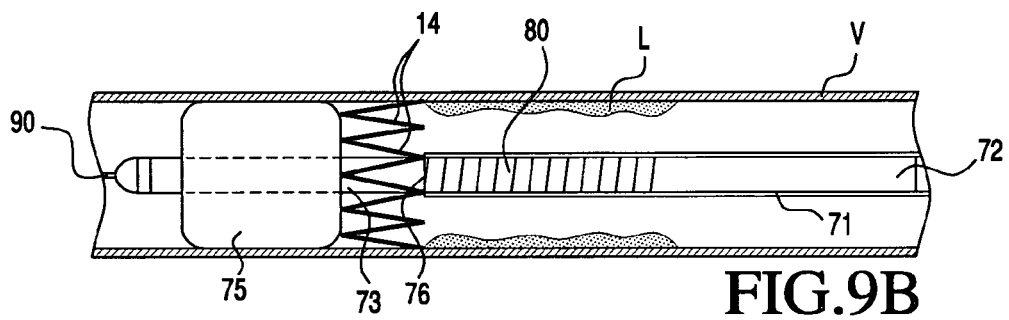

Referring to FIG. 9B, after balloon 75 is inflated to engage the vessel wall, sheath 71 is retracted proximally until distal section 81 self-expands into engagement with vessel wall within or distal to lesion L. Proximal movement of sheath 71 may be halted once radio-opaque marker 76 of sheath 71 is substantially aligned with radio-opaque marker 77 of inner member 72. When released from the constraint provided by sheath 71, the struts of distal section 81 expand in a radial direction to engage the interior of vessel V.

Figure 9C:
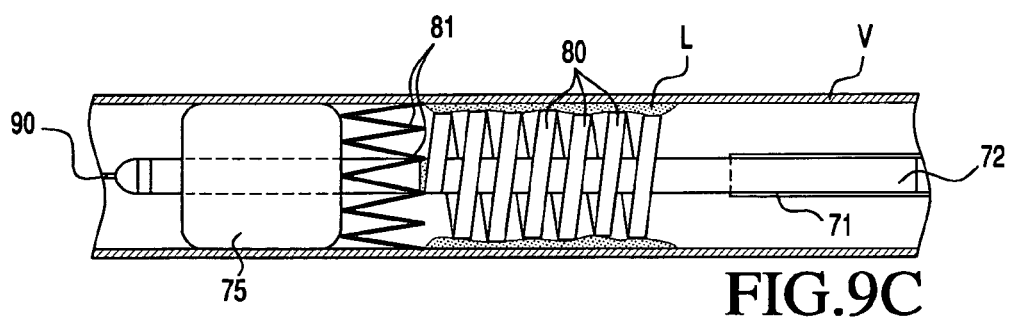
Figure 9D:
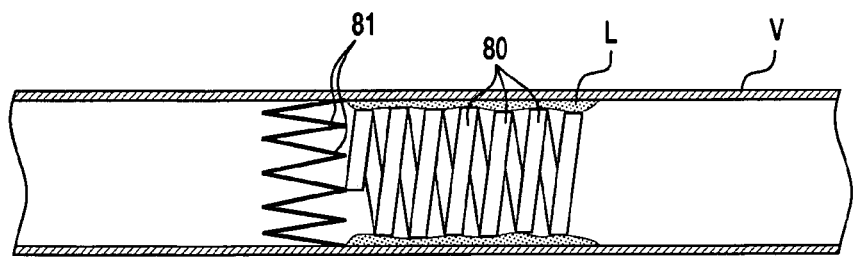

Referring now to FIG. 9C, after distal section 81 is secured to the vessel wall distal of lesion L, sheath 71 is further retracted proximally to cause the helical section of stent 80 to unwind and deploy to its predetermined shape within vessel V. During proximal retraction of sheath 71, the turns of the helical section of the stent unwind and engage and conform to an inner wall of vessel V in a controlled manner. Because inner member 72 includes a helical ledge (not shown) as described hereinabove with respect to FIGS. 5 and 6, the stent experiences little or no foreshortening. In addition, any forces that might be applied to distal section 81 during retraction of sheath 71 advantageously are uniformly distributed over the surface of balloon 75, thereby reducing the risk of insult to the vessel endothelium. Once the last turn of the helical section of stent 80 is deployed, balloon 75 is deflated, and the sheath optionally may be advanced to cover balloon 75. Delivery catheter 70 then is withdrawn from the patient's vessel, and guide wire 90 is removed.

While preferred illustrative embodiments of the invention are described above, it will be apparent to one skilled in the art that various changes and modifications may be made therein without departing from the invention. The appended claims are intended to cover all such changes and modifications that fall within the true spirit and scope of the invention.

What is claimed is:

1. A vascular prosthesis assembly comprising:
   a delivery device comprising:
   an elongate member; and
   a sheath over at least a portion of the elongate member;
   a vascular prosthesis comprising a self expanding helical portion, the helical portion placeable in a contracted, delivery state and an expanded, deployed state, the vascular prosthesis defining a central axis;
   the vascular prosthesis mounted on the elongate member in the contracted, delivery state with at least the helical portion located between the sheath and the elongate member;
   the helical portion comprising a continuous helical element extending along a helical path along the central axis in an axial direction and extending along the helical path completely around the central axis in a rotary direction in both the contracted, delivery state and the expanded, deployed state;
   the helical portion having a first wrap angle around said central axis and a first axial length along said central axis when in the contracted, delivery state;
   the helical portion having a second wrap angle around said central axis and a second axial length along said central axis when in the expanded, deployed state; and
   the first axial length being equal to the second axial length and the first wrap angle being equal to the second wrap angle.

2. The assembly according to claim 1, wherein the elongate member comprises:
   an outer surface;
   a helical ledge on the outer surface comprising at least one full turn; and
   the helical ledge having a third wrap angle equal to the first wrap angle; and wherein:
      the helical portion has a leading, distal edge and a trailing, proximal edge, the trailing, proximal edge contacting the helical ledge to aid in placement of the helical portion on the elongate member and to help maintain the helical portion in position relative to the elongate member when the sheath is moved proximally relative to the elongate member.

3. The assembly according to claim 1, wherein the vascular prosthesis comprises one self expanding helical portion.

4. The assembly according to claim 1, wherein the expanded, deployed state is a fully expanded state of the helical portion.

5. The assembly according to claim 1, wherein:
   the vascular prosthesis further comprises a self expanding anchor ring disposed distal of the helical portion; and
   the elongate member further comprises means for engaging the self expanding anchor ring to help prevent axial translation of the vascular prosthesis during proximal retraction of the sheath.

6. The assembly according to claim 5, wherein the means for engaging comprises a polymer layer that has been treated to enhance frictional engagement with the self expanding anchor ring.

7. The assembly according to claim 1, further comprising a balloon disposed adjacent to a distal end of the elongate member.

8. The assembly according to claim 1, further comprising means for engaging a wall of a vessel of a patient during deployment of the vascular prosthesis to help prevent axial displacement of the delivery device.

9. A method for assembling a vascular prosthesis assembly comprising:
   determining a target expanded diameter for a vascular prosthesis at a target site within a vessel of a patient;
   selecting a vascular prosthesis defining a central axis and having a self expanding helical portion;
   the helical portion comprising a continuous helical element extending along a helical path along the central axis in an axial direction and extending along the helical path completely around the central axis in a rotary direction in both the contracted, delivery state and the expanded, deployed state;
   selecting a first pitch;
   wrapping the vascular prosthesis onto an elongate member of a delivery device at the first pitch with the helical portion placed against the elongate member in a radially contracted state, the helical portion having a first axial length along said central axis and a first wrap angle around said central axis when in the contracted, delivery state;
   the helical portion having a second axial length along said central axis, a second pitch and a second wrap angle around said central axis when self expanded to the target expanded diameter;
   the first pitch selecting step carried out so that the first axial length is equal to the second axial length and the first wrap angle is equal to the second wrap angle; and
   placing a sheath over at least a portion of the helical portion.

10. The method according to claim 9, wherein:
    the selecting step further comprises selecting an elongate member having a substantially continuous helical ledge extending outwardly from an outer surface thereof, the helical ledge having a third wrap angle equal to the first wrap angle; and
    the wrapping step further comprises placing a trailing, proximal edge of the vascular prosthesis against the helical ledge.

11. A method for using a vascular prosthesis assembly comprising:
    selecting a vascular prosthesis assembly made according to the method of claim 9;
    placing a distal portion of the vascular prosthesis assembly at the target site;
    removing the sheath from at least the helical portion to permit the helical portion of the vascular prosthesis to expand towards the target expanded diameter; and
    removing the delivery device from the patient leaving the vascular prosthesis at the target site.

12. The method according to claim 11, wherein the sheath removing step is carried out by pulling the sheath proximally relative to the vascular prosthesis.

13. The method according to claim 9, wherein the wrapping step comprises wrapping the helical portion at least twice around the axis to create first and second complete helical turns, the helical turns having lateral edges.

14. The method according to claim 13, wherein the selecting step is carried out so that the lateral edges of the first and second helical turns are not attached to one another.

15. The assembly according to claim 1, wherein the helical portion extends at least twice around the central axis to define at least first and second complete helical turns.

16. The assembly according to claim 15, wherein the helical portion comprises:
    first and second edges extending in an axial direction and a rotary direction; and wherein:
       the first and second edges of the first helical turn are disconnected from the first and second edges of the second helical turn.

* * * * *